United States Patent
Watanabe et al.

(10) Patent No.: US 9,254,249 B2
(45) Date of Patent: Feb. 9, 2016

(54) ULTRAVIOLET ABSORBER

(71) Applicant: KAO CORPORATION, Chuo-ku (JP)

(72) Inventors: Takashi Watanabe, Katano (JP); Keigo Mikame, Suzuka (JP); Yasunori Ohashi, Soka (JP); Satoshi Sugawara, Chiba (JP); Kenzo Koike, Moka (JP)

(73) Assignee: KAO CORPORATION, Chuo-ku (JP)

( * ) Notice: Subject to any disclaimer, the term of this patent is extended or adjusted under 35 U.S.C. 154(b) by 195 days.

(21) Appl. No.: 14/119,705

(22) PCT Filed: Mar. 12, 2013

(86) PCT No.: PCT/JP2013/001593
§ 371 (c)(1),
(2) Date: Nov. 22, 2013

(87) PCT Pub. No.: WO2013/136770
PCT Pub. Date: Sep. 19, 2013

(65) Prior Publication Data
US 2014/0079653 A1    Mar. 20, 2014

(30) Foreign Application Priority Data

Mar. 13, 2012  (JP) ................................ 2012-056100

(51) Int. Cl.
| | | |
|---|---|---|
| *A61K 8/35* | (2006.01) | |
| *C08K 5/132* | (2006.01) | |
| *C09D 7/12* | (2006.01) | |
| *A61Q 17/04* | (2006.01) | |
| *C07C 49/255* | (2006.01) | |
| *C07C 49/84* | (2006.01) | |
| *C09D 5/00* | (2006.01) | |

(52) U.S. Cl.
CPC . *A61K 8/35* (2013.01); *A61Q 17/04* (2013.01); *C07C 49/255* (2013.01); *C07C 49/84* (2013.01); *C08K 5/132* (2013.01); *C09D 5/00* (2013.01); *C09D 7/1241* (2013.01)

(58) Field of Classification Search
None
See application file for complete search history.

(56) References Cited

U.S. PATENT DOCUMENTS 4,584,190 A    4/1986  Tejima et al.

FOREIGN PATENT DOCUMENTS

| JP | 60-109544 A | 6/1985 |
| JP | 63-166848 A | 7/1988 |
| JP | 08-113521 A | 5/1996 |
| JP | 11 209235 | 8/1999 |
| JP | 2000-328039 A | 11/2000 |
| JP | 2011 84493 | 4/2011 |

OTHER PUBLICATIONS

Written Opinion of the International Searching Authority Issued Jun. 28, 2013 in PCT/JP13/001593 Filed Mar. 12, 2013.
International Search Report Issued Jun. 28, 2013 in PCT/JP13/001593 Filed Mar. 12, 2013.
C. David Gutsche et al., "Experiments in the colchicine field. V. The thermal and photochemical decomposition of various 2-(β-Phenylethyl)-phenyldiazomethanes and 2-(ν-Phenyl-propyl)phenyldiazomethanes¹", Journal of the American Chemical Society, vol. 80, Nov. 5, 1958, pp. 5756-5767.
Masami Shimokoriyama, "Anthochlor pigments of *Coreopsis tinctoria*", Journal of the American Chemical Society, vol. 79, Jan. 5, 1957, pp. 214-220.

*Primary Examiner* — Robert A Wax
*Assistant Examiner* — Randeep Singh
(74) *Attorney, Agent, or Firm* — Oblon, McClelland, Maier & Neustadt, L.L.P.

(57) ABSTRACT

A compound represented by the following General Formula (1) is presented. Wherein, in the above General Formula (1), A is a single bond or —C=C— group.

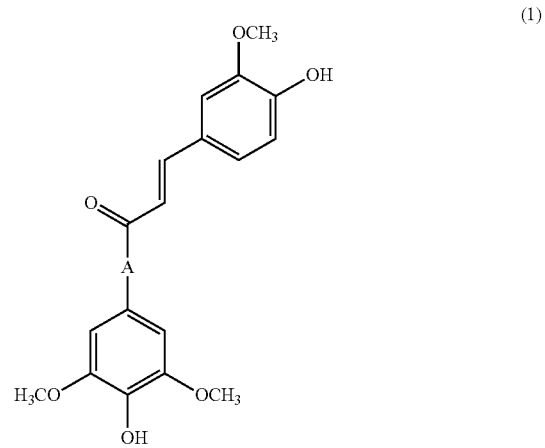

15 Claims, 7 Drawing Sheets

Normal phase HPLC analysis of CuO lignin Fr-5

Normal phase HPLC analysis of CuO lignin Fr-6

HPLC condition
Column: COSMOSIL 5-SL-II
Temp. RT
Eluent: n-Hexane/EtOH=30/30, 0.5 ml/min

Fr-4-2
$R_1=OCH_3, R_2=H$

| Position | δ H |
|---|---|
| 1 | |
| 2,6 | 7.23 2H,s |
| 3,5 | |
| 4 | |
| 1' | |
| 2' | 7.57 1H, d, J=1.6 |
| 3' | |
| 4' | |
| 5' | 6.81 1H, d, J=8.8 |
| 6' | 7.37 1H, dd, J=8.8,1.6 |
| 7 | |
| 7' | |
| 3,5-OCH$_3$ | 3.87 3H, s |
| 3'-OCH$_3$ | 3.94 3H, s |

Fr-4-3
$R1,R2=OCH_3$

| Position | δ H |
|---|---|
| 1 | |
| 2,6 | 7.23 2H,s |
| 3,5 | |
| 4 | |
| 7 | |
| 3,5-OCH$_3$ | 3.88 3H, s |

Fr-4-1
$R1,R2=H$

| Position | δ H |
|---|---|
| 2 | 7.56 2H, d, J=1.6 |
| 5 | 6.95 2H, d, J=8.8 |
| 6 | 7.37 2H, dd, J=8.8,1.6 |
| 3-OCH$_3$ | 3.94 3H, s |

| | Fr-5-1<br>R=H | | Fr-5-2<br>R=OCH₃ |
|---|---|---|---|

| Position | δ H | Position | δ H |
|---|---|---|---|
| 1 | | 1 | |
| 2 | 7.67 1H, d, J=1.9 | 2 | 7.47 1H, s |
| 3 | | 3 | |
| 4 | | 4 | |
| 5 | 6.93 1H, d, J=8.2 | 5 | |
| 6 | 7.75 1H, dd, J=8.2,1.9 | 6 | 7.47 1H, s |
| 7 | | 7 | |
| 8 | 7.72 1H, d, J=15.4 | 8 | 7.74 1H, d, J=15.5 |
| 9 | 7.74 1H, d, J=15.4 | 9 | 7.70 1H, d, J=15.5 |
| 1' | | 1' | |
| 2' | 7.47 1H, d, J=1.9 | 2' | 7.44 1H, d, J=1.8 |
| 3' | | 3' | |
| 4' | | 4' | |
| 5' | 6.89 1H, d, J=8.2 | 5' | 6.89 1H, d, J=8.2 |
| 6' | 7.29 1H, dd, J=8.1,1.9 | 6' | 7.31 1H, dd, J=8.2,1.8 |
| -OCH₃ | 3.93 6H, s | -OCH₃ | 3.92 9H, s |

Fr-6-1 R=H

| Position | δ C | δ H |
|---|---|---|
| 1,1' | | |
| 2,2' | | 7.31 1H, d, J=2.0 |
| 3,3' | | |
| 4,4' | | |
| 5,5' | | 6.84 1H, d, J=8.8 |
| 6,6' | | 7.19 1H, dd, J=8.8,2.0 |
| 7,7' | | 7.72 1H, d, J=15.6 |
| 8,8' | | 7.09 1H, d, J=15.6 |
| 9 | | |
| 3-OCH$_3$ | | 3.93 3H, s |

Fr-6-2 R=OCH$_3$

| Position | δ C | δ H |
|---|---|---|
| 1 | | |
| 2 | | 7.03 1H, s |
| 3 | | |
| 4 | | |
| 5 | | |
| 6 | | 7.03 1H, s |
| 7 | | 7.71 1H, dd, J=15.6,6.8 |
| 8 | | 7.13 1H, dd, J=15.6,8.8 |
| 9 | | |
| 1' | | |
| 2' | | 7.31 1H, d, J=2.0 |
| 3' | | |
| 4' | | |
| 5' | | 6.83 1H, d, J=8.8 |
| 6' | | 7.19 1H, dd, J=8.8,2.0 |
| 7' | | 7.74 1H, dd, J=15.6,6.8 |
| 8' | | 7.09 1H, dd, J=15.6,8.8 |
| 3,5-OCH$_3$ | | 3.91 6H, s |
| 3'-OCH$_3$ | | 3.93 3H, s |

(a)

(b)

ULTRAVIOLET ABSORBER

TECHNICAL FIELD

The present invention relates to an ultraviolet (UV) absorber.

BACKGROUND ART

Ultraviolet (UV), which is contained in sunlight, is a light having wavelengths that are shorter than wavelengths of visible light that human being can sense. Components of UV, which can reach to the surface of the earth, are classified into UV-A having wavelengths of 320 to 400 nm (long wavelength UV) and UV-B having wave lengths of 290 to 320 nm (medium wavelength UV). Radiation of such UV causes deteriorations of industrial products such as a breaking of plastic materials, discoloration of paints and the like, as well as causing unignorable damages to human skins.

On the other hand, the concepts for emphasizing the environmental protection and the safety are propagating throughout the world, and applied researches for utilizing biomass, which is typical environmental cycling process, are actively conducted. Lignin is a nature biomass, which, as well as cellulose and hemicellulose, constitutes a plant, and constitutes about 20 to 35% of a lumber. A number of herbaceous plants also include lignin. Lignin provides improved physical strength to the plant cell walls, as well as serving functions for preventing degradations by living substances and/or serving functions for controlling flowability of water by providing hydrophobicity to cell walls. Lignin is an irregular polymer, which has parahydroxyphenyl propane as its basic skeleton and is created by dehydrogenative polymerization of a monolignol having 0 to 2 methoxyl group(s), namely p-coumaryl alcohol, coniferyl alcohol or sinapyl alcohol.

The use of such lignin as a raw material of a UV absorber is examined (Patent Literature 1, Non-Patent Literature 1).

Patent Literature 1 describes that a lignin, which is separated and extracted from a plant material by utilizing microwave and microwave-sensitized catalyst, is employed as a UV absorber.

Non-Patent Literature 1 discloses a report related to dimers contained in degradation product of lignin by CuO oxidation.

CITATION LIST

Patent Literature

PTL 1: Japanese Patent Publication No. JP-A-2011-84,493

Non Patent Literature

NPL 1: Irwin A. Pearl and Edgar E. Dickey, "Studies on Lignin and Related Products. VII. The Isolation of Certain Compounds from Lignin Oxidation Mixtures by Chromatographic Techniques", J. Am. Chem. Soc., 1952, 74 (3), pp 614-617

SUMMARY OF INVENTION

According to one aspect of the present invention, a compound represented by the following General Formula (1) is presented.

[Chem. 1]

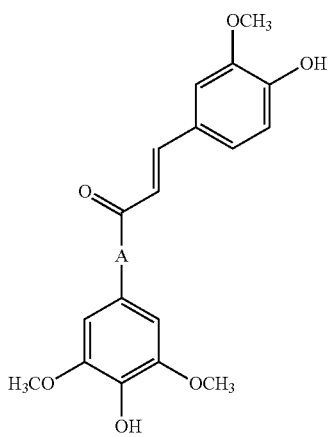

(1)

Wherein, in the above General Formula (1), A is a single bond or —C=C— group.

BRIEF DESCRIPTION OF DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DESCRIPTION OF EMBODIMENTS

Figure 1:
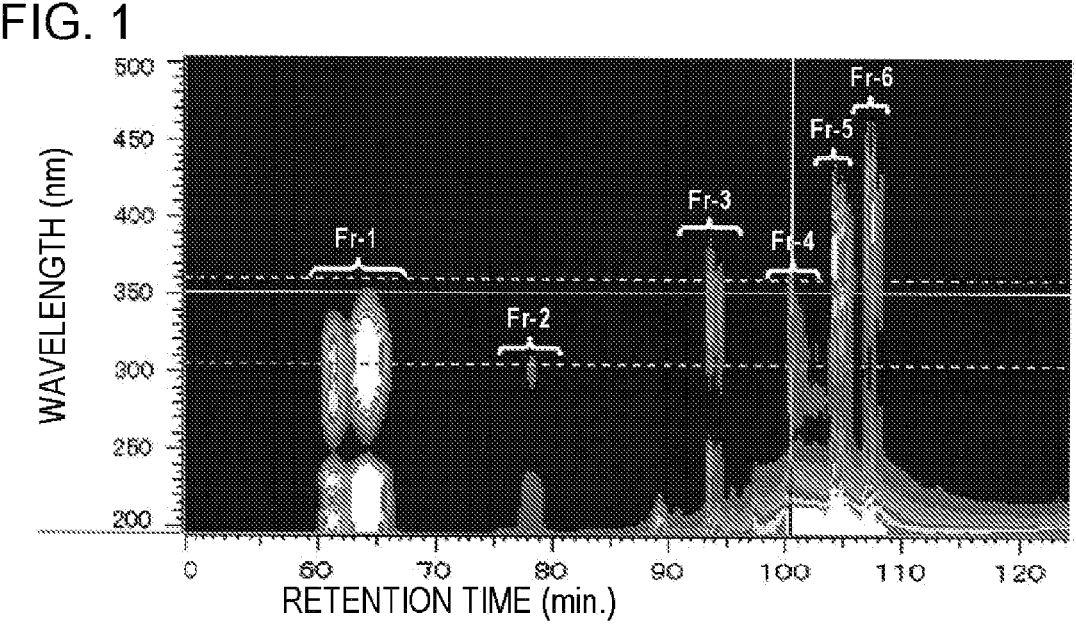
FIG. 1 is a chart, showing a result of reversed phase high performance liquid chromatography (HPLC) analysis of low molecular weight lignin fraction (ACSL fraction) through a copper oxide-degradation in Example 1.

The following examples further describe and demonstrate embodiments of the present invention. The examples are given solely for the purpose of illustration and are not to be construed as limitations of the present invention.

The present embodiment relates to provide a novel UV absorber.

According to the present embodiment, a new UV absorber can be provided.

Compounds according to the present embodiment are compounds represented by the above-described General Formula (1), and more specifically are compounds represented by the following Formula (1-1) or Formula (1-2).

[Chem. 2]

(1-1)

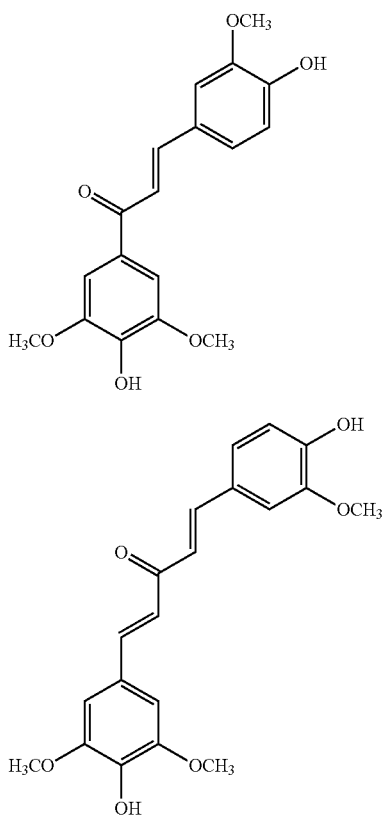

(1-2)

As will be discussed later in the description of Examples, each of the above-described compounds exhibits specific wavelengths for absorbing radiation in the ultraviolet range, and more specifically, exhibits enhanced effect of absorbing ultraviolet ray included in the UV-A range of 320 to 400 nm. Thus, the above-described compounds can be effectively utilized as UV absorbers.

The UV absorber according to the present embodiment contains one, two or more compound(s) selected from the group consisting of the compound represented by the above General Formula (1), a compound represented by the following General Formula (2), a compound represented by the following General Formula (3) and a compound represented by the following General Formula (4).

[Chem. 3]

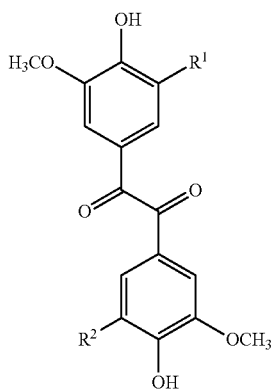

(2)

Wherein, in the above General Formula (2), $R^1$ and $R^2$ are a hydrogen atom or —$OCH_3$ group, and are mutually independent.

[Chem. 4]

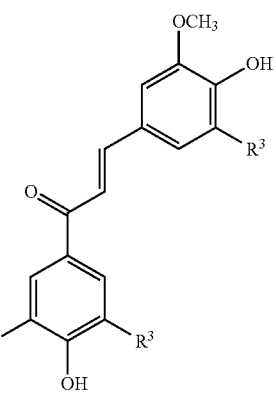

(3)

Wherein, in the above General Formula (3), $R^3$ is a hydrogen atom or —$OCH_3$ group.

[Chem. 5]

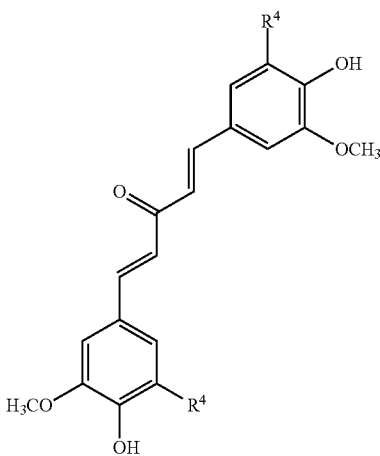

(4)

Wherein, in the above General Formula (4), $R^4$ is a hydrogen atom or —$OCH_3$ group.

Specific example of the UV absorber according to the present embodiment may include any of the compounds represented by the above Formula (1-1) or Formula (1-2).

Further, the UV absorber according to the present embodiment may contain the compound represented by the above General Formula (1) and other component. For example, the UV absorber according to the present embodiment may further contain, in addition to the compound represented by the above General Formula (1), one, two or more compound(s) selected from the group consisting of the compounds represented by the above General Formulae (2), (3) and (4).

The use of the combination of the compound represented by the above General Formula (1) and one or more of the compounds represented by the above General Formulae (2), (3) and (4) allows more stably obtaining the ultraviolet absorption effect over broader wavelength range. In addition, since the compounds represented by the above General Formulae (2), (3) and (4) can be obtained by the same production process as employed in the production of the compound represented by the above General Formula (1) as will be discussed later, the use of such combination can also provide improved facility for the production of the UV absorber.

The UV absorber of the present embodiment may contain one or two compounds selected from the group consisting of the following compounds Fr-5-2 and Fr-6-2.

In addition, the UV absorber of the present embodiment may contain one or two compounds selected from the group consisting of the following compounds Fr-5-2 and Fr-6-2 and further contain one, or two or more compounds selected from the group consisting of the following compounds Fr-4-1, Fr-4-2, Fr-4-3, Fr-5-1 and Fr-6-1.

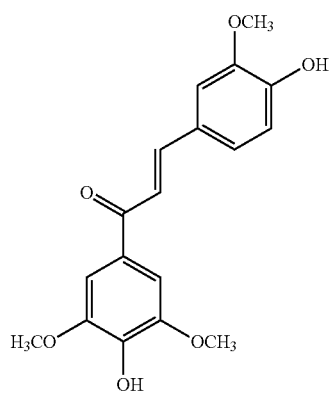
(Fr-5-2)

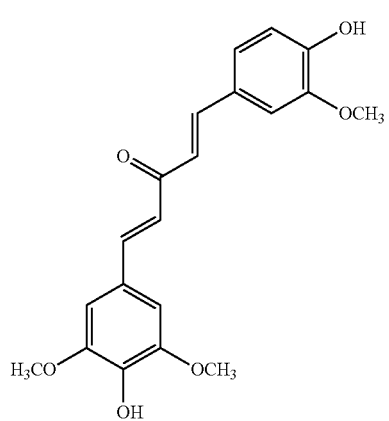
(Fr-6-2)

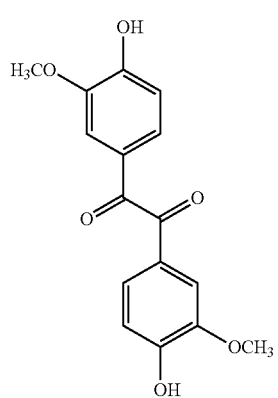
(Fr-4-1)

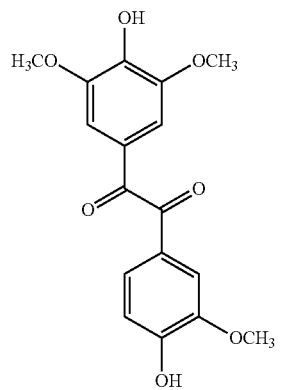
(Fr-4-2)

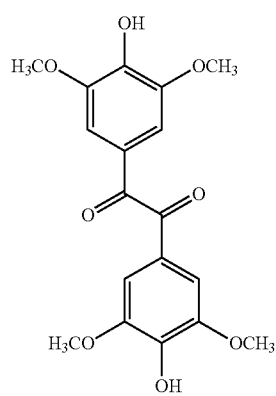
(Fr-4-3)

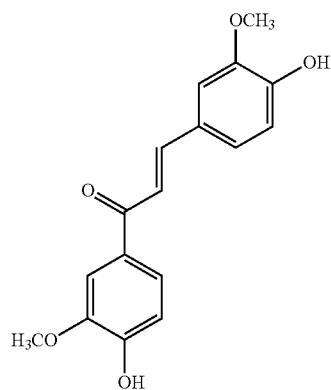
(Fr-5-1)

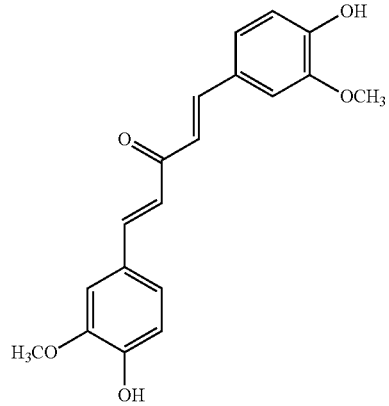
(Fr-6-1)

More specifically, the UV absorber of the present embodiment may contain the above compounds Fr-5-2 and Fr-6-2.

The UV absorber of the present embodiment may contain the above compounds Fr-6-2 and Fr-4-1.

The UV absorber of the present embodiment may contain the above compounds Fr-5-2 and Fr-4-1.

The UV absorber of the present embodiment may contain the above compounds Fr-6-2 and Fr-4-2.

The UV absorber of the present embodiment may contain the above compounds Fr-5-2 and Fr-4-2.

The UV absorber of the present embodiment may contain the above compounds Fr-6-2 and Fr-4-3.

The UV absorber of the present embodiment may contain the above compounds Fr-5-2 and Fr-4-3.

The UV absorber of the present embodiment may contain the above compounds Fr-6-2 and Fr-5-1.

The UV absorber of the present embodiment may contain the above compounds Fr-5-2 and Fr-5-1.

The UV absorber of the present embodiment may contain the above compounds Fr-6-2 and Fr-6-1.

The UV absorber of the present embodiment may contain the above compounds Fr-5-2 and Fr-6-1.

The UV absorber of the present embodiment may contain the above compounds Fr-5-2, Fr-4-1, Fr-4-2 and Fr-4-3.

The UV absorber of the present embodiment may contain the above compounds Fr-6-2, Fr-4-1, Fr-4-2 and Fr-4-3.

In the next, the process for producing the compounds represented by the above General Formulae (1) to (4) will be described.

The compounds represented by the above General Formulae (1) to (4) are obtained by, for example, degradation, separation and extraction from a plant material containing lignocellulose. More specifically, a typical process for obtaining such compounds may include: a process for supplying a plant material containing lignocellulose and an oxidation catalyst such as copper oxide and the like in a pressure vessel and heating the vessel to a temperature of about 20 to 300 degrees C.; and a process, in which an oxidation catalyst such as copper oxide and the like is added to a plant material containing lignocellulose and a microwave treatment involving local radiation with controllable output is conducted in short time. Such processes allow effective preparations of the UV absorption compounds, which can absorb UV radiation over the longer wavelength range, so that the preparations of the compounds that are unique to the lignin degradation products can be achieved.

Processes utilizing the microwave processing will mainly be described as exemplary implementations in the following descriptions.

In the above-described production process, available plant materials are not limited to any specific material, as long as the plant contains lignocellulose, and typical plant materials include: wood materials such as softwood, hardwood, and the like; non-wood type lignocelluloses and the like.

More specifically, typical softwood materials include: *Cryptomeria japonica* (Cryptomeria); *Picea jezoensis* (Yezo spruce); *Larix Leptolepis* (Larix kaempferi, Japanese larch); *Pinus Thunbergii* (Japanese black pine); *Abies sachalinensis* (Sakhalin fir); *Pinus parviflora* (Japanese white pine); *Taxus cuspidata* (Spreading yew); *Thuja Standishii* (Japanese thuja); *Picea torano* (Tiger-tail spruce); *Picea alcokiana* (Alcock's spruce); *Podocarpus macrophyllus* (Japanese yew); *Abies firma* (fir); *Chamaecyparis pisifera* (Sawara cypress); *Pseudotsuga japonica* (Japanese Douglas fir); *Thujopsis dolabrata* (Hiba arborvitae); *Thujopsis dolabrata* var. *hondae*; *Tsuga sieboldii* (Southern Japanese hemlock); *Tsuga diversifolia* (Northern Japanese hemlock); *Chamaecyparis obtusa* (Hinoki cypress); *Cephalotaxus harringtonia* (Cowtail pine); *Picea jezoensis* (Japanese spruce); *Callitropsis nootkatensis* (Yellow cedar); *Chamaecyparis lawsonia* (Lawson cypress); *Pseudotsuga menziesii* (Douglas fir); *Picea sitchensis* (Sitka spruce); *Pinus radiata* (Monterey pine); *Picea rubens* (Eastern spruce, Red spruce); *Pinus strobus* (Eastern white pine); *Larix occidentalis* (Western Larch); *Abies concolor* (Western fir); *Tsuga heterophylla* (Western hemlock); *Larix laricina* (Tamarack larch), and the related wood species.

On the other hand, typical hardwood materials include: *Fagus crenata* (Siebold's beech, Japanese beech), *Robinia pseudoacacia* (Acacia), Paraserianthes falcataria (Albizia), *Betula platyphylla* (Japanese birch), *Populus Tremuloides* (Aspen), *Prunus serotina* (American black cherry), *Liriodendron* (Yellow poplar, Tulip poplar), *Juglans regia* (Walnut), *Betula* (Birch), *Zelkova serrata* (Japanese zelkova, Keyaki), *Acer pseudoplatanus* (sycamore maple), *Betula alnoides* (Chinese cherry), *Fraxinus mandshurica* (Manchurian Ash), *Tectona grandis* (Teak), *Ulmus parvifolia* (Chinese elm), *Acer truncatum* (Chinese maple), *Quercus crispula* (Quercus dentata, Quercus serrata, Japanese oak), *Acer nigrum* (Hard maple, Black maple), *Carya glabra* (*Carya* spp., Hickory), *Carya illinoinensis* (Pecan), *Fraxinus americana* (White ash), *Quercus alba* (White oak), *Betula papyrifera* (American white birch), *Quercus coccinea* (Red oak, Scarlet oak), and the related wood species.

Further, typical non-wood type materials include: agricultural products such as rice, sugar cane, wheat, corn, pineapple, oil palm and the like, and their wastes; industrial plants such as kenaf, cottons and the like, and their wastes; forage crops such as alfalfa, timothy and the like; bamboos; bamboo grasses; and the like.

Among these, wood materials such as softwood materials, hardwood materials are preferable, in view of providing enhanced extraction efficiency.

The shapes of these plant materials are not limited, and any types of shape such as powders, chip-like shapes, squared lumber-like shapes, round wood-like shapes, flakelike shapes, fiber-like shapes (having dimensions of, for example, length of around 0.5 to 3 cm and diameter of around 0.01 to 2 mm) and the like may be available. In view of achieving degradation and extraction of lignin from the plant material with improved efficiency, it is preferable to employ powders, chip-like shapes, and flakelike shapes, which provide larger surface area.

For the solvent used in separating and extracting lignin from the plant material containing the lignocellulose, it is preferable to employ water, or polyol of 2 to 5 of carbon atoms or monohydric alcohol of 1 to 8 of carbon atoms, which are easily miscible with water, or the mixtures thereof, in views of providing easy dispersion of the plant material, providing easy extraction of lignin, achieving reduced environmental load, and the like. Typical polyols of 2 to 5 of carbon atoms include, for example, propylene glycol, butylene glycol, ethylene glycol and glycerol, and typical monohydric alcohols of 1 to 8 of carbon atoms include, for example, ethanol, propanol, and butanol. One of these may be employed alone, or a mixture of two or more of these may also be employed. A mixture of water and polyol of 2 to 5 of carbon atoms or monohydric alcohol of 1 to 8 of carbon atoms is more preferable. In this case, it is preferable to prepare such mixture by adding 0.1 to 10 parts by weight of the organic solvent to 1 part by weight of water. While the weight ratio of the employed plant material and the solvent is not limited, the preferable ratio is: plant material: solvent=1:1 to 1:100, and more preferably preferable ratio is: plant material:solvent=1:5 to 1:30. The ratio within the above-described range allows achieving a higher heating rate and an effective processing of the plant material.

A microwave-sensitized catalyst may be employed for an oxidation catalyst. The microwave-sensitized catalyst is employed for providing energy to the plant material with improved efficiency, and for example, salt of metallic element and halogen, salt of metallic element and sulfuric acid, salt of metallic element and organic carboxylic acid, and metallic oxide may be employed for the microwave-sensitized catalyst. More specifically, the available compounds for the microwave-sensitized catalyst includes: compounds of aluminum such as aluminum fluoride, aluminum chloride, aluminum bromide, aluminum iodide, aluminum sulfate, aluminum oxide and the like; compounds of copper such as copper (I) fluoride, copper (II) fluoride, copper (I) chloride, copper (II) chloride, copper (I) bromide, copper (II) bromide, copper (I) iodide, copper (II) iodide, copper (I) sulfate, copper (II) sulfate, copper (I) oxide, copper (II) oxide and the like; compounds of iron such as iron fluoride (II), iron fluoride (III), iron (II) chloride, iron (III) chloride, iron (II) bromide, iron (III) bromide, iron (II) iodide, iron (III) iodide, iron (II) sulfate, ion (III) sulfate, iron (II) oxide, iron (III) oxide and the like; compounds of zinc such as zinc fluoride, zinc chloride, zinc bromide, zinc iodide, zinc sulfate, zinc oxide and the like; compounds of silver such as silver fluoride, silver chloride, silver bromide, silver iodide, silver oxide and the like; compounds of boron such as boron fluoride, boron chloride, boron oxide and the like; compounds of titanium such as titanium (IV) chloride, titanium (IV) oxide (titanium dioxide) and the like; compounds of nickel such as nickel chloride and the like; compounds of scandium such as scandium trifluoromethanesulfonate and the like; compound of yttrium such as yttrium chloride and the like; compounds of lanthanoids such as cerium chloride, neodymium chloride and the like; compounds of palladium; compounds of vanadium; compounds of mercury such as mercury oxide and the like; compounds of cobalt such as cobalt oxide and the like. Among these, salt of metallic element and halogen, salt of metallic element and sulfuric acid, and metallic oxide are preferable, for the reason that the waste liquid thereof can be easily processed to achieve reduced environmental load, and that these are available to obtain at lower cost, and more specifically, aluminum chloride, aluminum bromide, aluminum sulfate, aluminum oxide, copper (II) oxide, silver oxide, mercury oxide, cobalt oxide, iron (III) chloride, iron (III) oxide, zinc chloride, zinc bromide, zinc sulfate, zinc oxide and titanium (IV) oxide are preferable.

Alternatively, nitrobenzene, potassium permanganate and the like may also be employed for the oxidation catalyst.

One of these microwave-sensitized catalysts may be employed alone, or a mixture of two or more of these microwave-sensitized catalysts may also be employed, and the additive quantity of the catalyst is preferably 1 to 1,000 micro-mol over 1 g of the plant material, and more preferably 30 to 720 micro-mol over 1 g of the plant material, and further preferably 50 to 360 micro-mol over 1 g of the plant material. The additive quantity within such ranges provides sufficient effect of the separation of saccharide and lignin, so that easy processing of the solvent after the reaction is achieved. From the above viewpoint, the additive quantity of the catalyst over 1 g of the plant material is preferably 1 micro-mol or larger more preferably 30 micro-mol or larger and further preferably 50 micro-mol or larger. Also, the additive quantity of the catalyst over 1 g of the plant material is preferably 1,000 micro-mol or smaller, more preferably 720 micro-mol or smaller and further preferably 360 micro-mol or smaller.

The exposure to the microwave may be conducted by an ordinary method, and it is preferable to expose to microwave having frequency of around 300 to 30,000 MHz, preferably around 2,000 to 6,000 MHz, in view of permeability and attenuating absorption of the microwave for the plant material. From the above viewpoint, the frequency of the microwave is preferably 300 MHz or larger and more preferably 2,000 MHz or larger. Also, the frequency of the microwave is preferably 30,000 MHz or smaller and more preferably 6,000 MHz or smaller. While the reaction time by the exposure to the microwave is not limited, the preferable reaction time is 30 seconds to 60 minutes, and more preferable reaction time is 10 to 30 minutes. The time for exposing to the microwave within the above-described range allows sufficient separation of saccharides and lignin, so that unwanted degradations of useful chemical substances can be inhibited. From the above viewpoint, the reaction time by the exposure to the microwave is preferably 30 seconds or longer and more preferably 10 minutes or longer. Also, the reaction time by the exposure to the microwave is preferably 60 minutes or shorter and more preferably 30 minutes or shorter.

The preferable temperature during the exposure to the microwave may be 80 to 240 degrees C., and preferably 150 to 180 degrees C., in view of sufficiently separating and extracting lignin from lignocellulose without degrading other components. From the above viewpoint, the temperature during the exposure to the microwave is preferably 80 degrees C. or higher and more preferably 150 degrees C. or higher. Also, the temperature during the exposure to the microwave is preferably 240 degrees C. or lower and more preferably 180 degrees C. or lower.

Such separation and extraction of lignin may be preferably conducted in the state where the liquid is contained within a sealed pressure vessel. The pressure in such state is determined based on the vapor pressure during the reaction, and the pressure may be suitably adjusted for the purpose of controlling the decomposition and the extraction. For example, when the mixing ratio by weight of solvent:water is (9:1) and the mixing ratio by weight of solvent:water is (1:1), the suitable pressure may be about 7 atm to about 18 atm for the condition that the reaction temperature is 180 degrees C., while these may be varied depending on the type of the solvent.

Lignin can be separated and extracted from lignocellulose into the solvent by the above-described method. Thus obtained lignin contains specific structures in molecule, which are effectively broken and/or bound, so as to provide the molecular weight of the isolated lignin of 150 to 1,000,000, preferably around 500 to 100,000. That is, the molecular weight of the isolated lignin is preferably 150 or larger and more preferably 500 or larger. Also, the molecular weight of the isolated lignin is preferably 1,000,000 or smaller and more preferably 100,000 or smaller.

Since lignin extracted in such process contains a compound represented by the above General Formula (1), such lignin exhibits enhanced ultraviolet absorption effect, and thus can be employed for a UV absorber. Further, lignin containing the compounds represented by the above General Formulae (2) to (4) as well as containing the compound represented by the above General Formula (1) may also be obtained.

Alternatively, as have been described above, the separation and the extraction of lignin may also be achieved by employing a method for heating the plant material and the solvent, without employing the microwave-sensitized catalyst or without utilizing the exposure to the microwave.

The UV absorber according to the present embodiment can be obtained by the above-described method. The form of the obtained UV absorber is not limited to any specific morphology. For example, the solvent may be preferably selected to provide the morphology for the use such as: an extracted state obtained by simply filtering to remove the plant material; or a state of concentrated liquid or slurry; or powder obtained by conducting the filtration and the drying. Further, these may be isolated and refined by an ordinary method as required.

Since the UV absorber according to the present embodiment contains the compound represented by the above General Formula (1), such UV absorber may be, for example, added to a paint or a plastic material and the like to provide prevention for the optical deterioration thereof, and may also be added to a cosmetic product or a hair care product to provide prevention for the optical damage of the skin and the hair.

The UV absorber according to the present embodiment is applicable to a cosmetic. Examples of the cosmetic containing the UV absorber of the present embodiment include a skin cosmetic such as a sunscreen cosmetic; and a hair cosmetic. An existing form of the cosmetic may be selectable from liquid, gel, emulsion, and so forth.

Also, the UV absorber according to the present embodiment is applicable to, for example, an UV-absorbing container, a resin composition, a coating agent or a paint composition.

Regarding the above embodiments, the present invention further discloses the following compositions, production processes or uses.

1. A compound represented by the following General Formula (1).

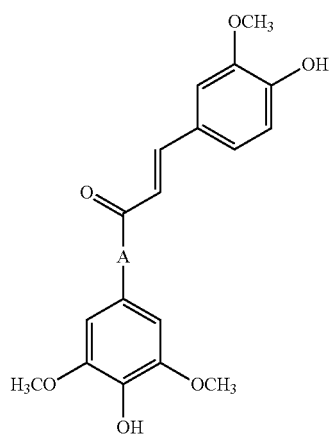

(1)

Wherein, in the above General Formula (1), A is a single bond or —C=C— group.

2. An ultraviolet (UV) absorber, containing the compound according to the above 1.

3. An ultraviolet (UV) absorber, containing one, two or more compound(s) selected from the group consisting of the compound represented by the following General Formula (1), a compound represented by the following General Formula (2), a compound represented by the following General Formula (3) and a compound represented by the following General Formula (4).

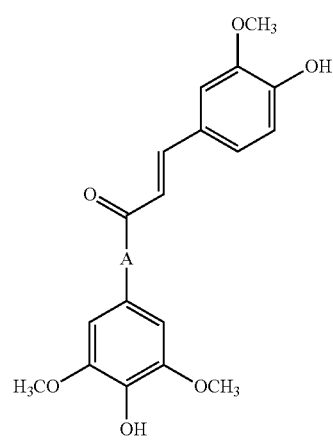

(1)

Wherein, in the above General Formula (1), A is a single bond or —C=C— group.

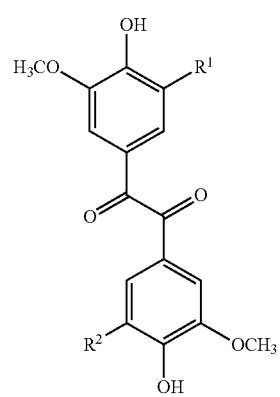

(2)

Wherein, in the above General Formula (2), $R^1$ and $R^2$ are a hydrogen atom or —$OCH_3$ group, and are mutually independent.

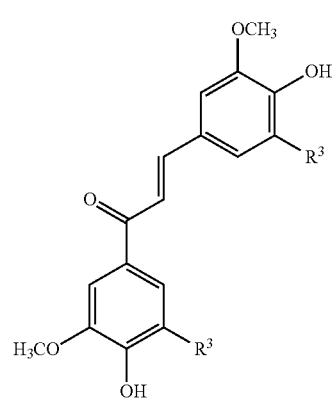

(3)

Wherein, in the above General Formula (3), $R^3$ is a hydrogen atom or —$OCH_3$ group.

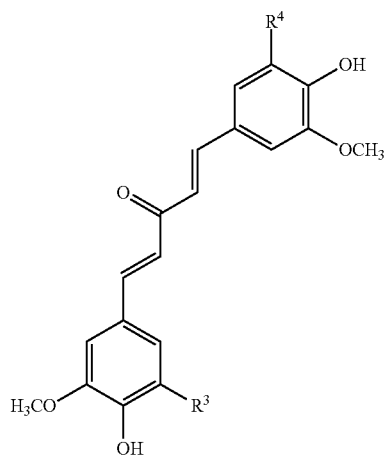

(4)

Wherein, in the above General Formula (4), $R^4$ is a hydrogen atom or —$OCH_3$ group.

4. The UV absorber according to the above 2. or 3., containing the following compounds Fr-5-2 and Fr-6-2.
5. The UV absorber according to the above 2. or 3., containing the following compounds Fr-6-2 and Fr-4-1.
6. The UV absorber according to the above 2. or 3., containing the following compounds Fr-5-2 and Fr-4-1.
7. The UV absorber according to the above 2. or 3., containing the following compounds Fr-6-2 and Fr-4-2.
8. The UV absorber according to the above 2. or 3., containing the following compounds Fr-5-2 and Fr-4-2.
9. The UV absorber according to the above 2. or 3., containing the following compounds Fr-6-2 and Fr-4-3.
10. The UV absorber according to the above 2. or 3., containing the following compounds Fr-5-2 and Fr-4-3.
11. The UV absorber according to the above 2. or 3., containing the following compounds Fr-6-2 and Fr-5-1.
12. The UV absorber according to the above 2. or 3., containing the following compounds Fr-5-2 and Fr-5-1.
13. The UV absorber according to the above 2. or 3., containing the following compounds Fr-6-2 and Fr-6-1.
14. The UV absorber according to the above 2. or 3., containing the following compounds Fr-5-2 and Fr-6-1.
15. The UV absorber according to the above 2. or 3., containing the following compounds Fr-5-2, Fr-4-1, Fr-4-2 and Fr-4-3.
16. The UV absorber according to the above 2. or 3., containing the following compounds Fr-6-2, Fr-4-1, Fr-4-2 and Fr-4-3.

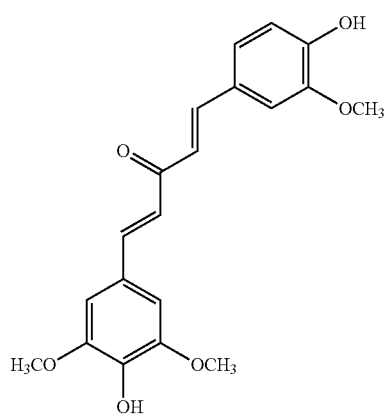

(Fr-6-2)

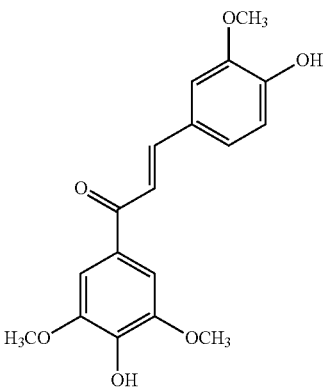

(Fr-5-2)

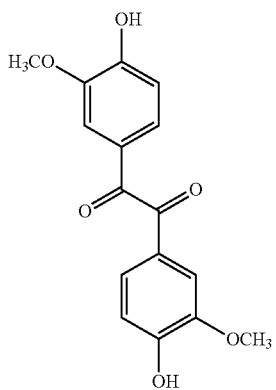

(Fr-4-1)

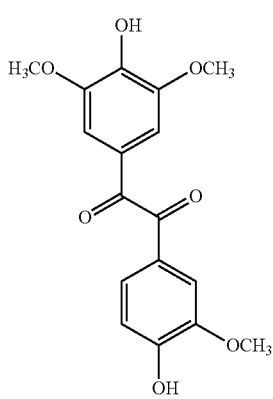

(Fr-4-2)

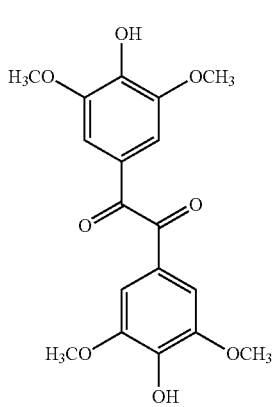

(Fr-4-3)

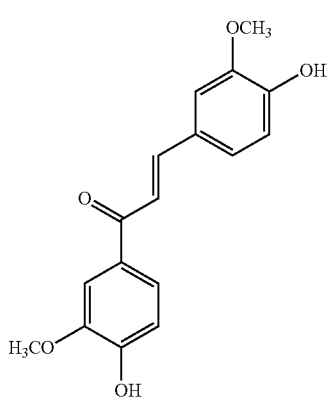

(Fr-5-1)

(Fr-6-1)

17. A cosmetic containing the UV absorber according to any one of the above 2. to 16.

18. A use of the UV absorber according to any one of the above 2. to 16. as a cosmetic containing the UV absorber.

19. A use of the UV absorber according to any one of the above 2. to 16. as an UV-absorbing container containing the UV absorber.

20. A use of the UV absorber according to any one of the above 2. to 16. as a resin composition containing the UV absorber.

21. A use of the UV absorber according to any one of the above 2. to 16. as a coating agent containing the UV absorber.

22. A use of the UV absorber according to any one of the above 2. to 16. as a paint composition containing the UV absorber.

23. A process for preparing the UV absorber according to any one of the above 2. to 16., containing
adding a softwood material or a hardwood material to the solvent of a mixture of water and polyol of 2 to 5 of carbon atoms or monohydric alcohol of 1 to 8 of carbon atoms; and then
exposing a microwave thereto and obtaining the UV absorber.

24. A process for preparing the UV absorber according to any one of the above 2. to 16., containing
adding a softwood material or a hardwood material and a microwave-sensitized catalyst to the solvent of a mixture of water, polyol of 2 to 5 of carbon atoms or monohydric alcohol of 1 to 8 of carbon atoms; and then exposing a microwave thereto and obtaining the UV absorber.

EXAMPLES

The following examples further describe and demonstrate embodiments of the present invention. The examples are given solely for the purpose of illustration and are not to be construed as limitations of the present invention. Also, while the present invention will be further described in detail in reference to Examples, it is not intended to limit the scope of the present invention thereto.

Example 1

In the present Example, respective compounds were obtained by copper oxide degradation of lignocellulose materials.

(Copper Oxide Degradation Processing)

Fraction of the crushed materials of the Siebold's beech (*Fagus crenata*) having particle diameters corresponding to 14 to 30 mesh sieves (Japanese Industrial Standards) and fraction thereof passing through 42 mesh sieve were employed as the wood powder.

1.0 g of each of the wood powder samples, 0.5 g of CuO and 20 mL of 1N NaOH aqueous solution were introduced to a pressure tight glass vessel, and after the seal was provided, the vessel was exposed to the microwave of 2,450 MHz at 180 degrees C. for 30 minutes by using a microwave processing apparatus. The resultant processed liquid was cooled, and then, a centrifugal separation process (employing CF25RXII, commercially available from Hitachi Co., Ltd., 6,000 rpm, for 3 minutes) and a reduced pressure filtration process were conducted to achieve a separation into an alkaline-soluble fraction and an insoluble fraction. The insoluble fraction was rinsed, and then was freeze-dried to be recovered as an alkaline-insoluble fraction (hereinafter referred to as "ALIS").

The alkaline-soluble fraction was further treated with 1N HCl to adjust its acidity as pH 1.5, and then the centrifugal separation process (employing CF25RXII, commercially available from Hitachi Co., Ltd., 6,000 rpm, for 3 minutes) and the reduced pressure filtration process were conducted to achieve a separation into a soluble fraction and an insoluble fraction. The insoluble fraction was rinsed, and then was freeze-dried to be recovered as an acid-insoluble fraction containing polymer lignin fraction (hereinafter referred to as "ACIS").

An extraction with ethyl acetate was conducted for the soluble fraction to obtain a low molecular weight lignin fraction (hereinafter referred to as "ACSL"). Yields of the respective fractions are shown in Table 1.

TABLE 1

MATERIAL BALANCE OF COPPER OXIDE DEGRADED PRODUCTS OF *FAGUS CRENATA*

| | ALIS (RESIDUE) | ACIS (HIGH MOLECULAR WEIGHT) | ACSL (LOW MOLECULAR WEIGHT) |
|---|---|---|---|
| *FAGUS CRENATA* 14-30 MESH (1 g) | 984 mg | 30.3 mg | 34.6 mg |
| *FAGUS CRENATA* 42 MESH PASS (1 g) | 910 mg | 187 mg | 99.8 mg |

(Analysis of Low Molecular Weight Lignin Fraction (ACSL) through Copper Oxide-Degradation)

The obtained ACSL was dissolved in methanol (MeOH), and then the reversed phase high performance liquid chromatography (HPLC) was utilized to separate respective fractions Fr-1 to Fr-6 having UV absorption bands. The results of the HPLC are shown in FIG. 1. The yields of the respective fractions are shown in Table 2. Further, the conditions for the HPLC were as follows.

(HPLC Conditions)

Column: COSMOSIL AR-II (commercially available from NACALAI TESQUE, INC.) 20×250 mm;

Eluent: methanol/water.

TABLE 2

YIELDS OF LOW MOLECULAR WEIGHT LIGNIN FRACTION (ACSL) THROUGH COPPER OXIDE-DEGRADATION

| FRACTION No. | YIELD/% (PER WOOD WEIGHT) |
|---|---|
| Fr-1 | 3.5 |
| Fr-2 | 0.4 |
| Fr-3 | 0.5 |
| Fr-4 | 1.0 |
| Fr-5 | 1.5 |
| Fr-6 | 0.9 |

According to the results of the reversed phase liquid chromatography-mass spectrometry (LC-MS) analysis for Fr-1 and Fr-3, it was found that Fr-1 contained syringaldehyde and vanillin as its major constituents. It was also found that Fr-3 contained 4-(4-Hydroxy-3-methoxyphenyl)-3-buten-2-one as its major constituent. The compounds detected in Fr-1 and Fr-3 are presented by the following formulae.

[Chem. 6]

[Chem. 7]

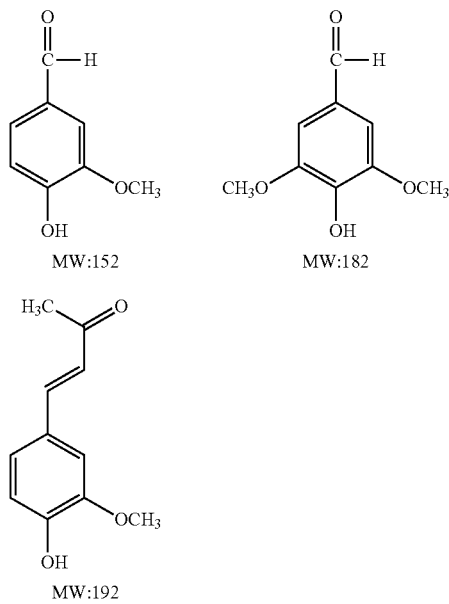

Besides, purifications were conducted for Fr-4, Fr-5 and Fr-6 by utilizing the normal phase HPLC. The conditions for the purification were as follows.

(Conditions for Separations)

Column: COSMOSIL SL-II (commercially available from NACALAI TESQUE, INC.) 4.6×250 mm;

Eluent: hexane/ethanol=80/20.

Figure 2:
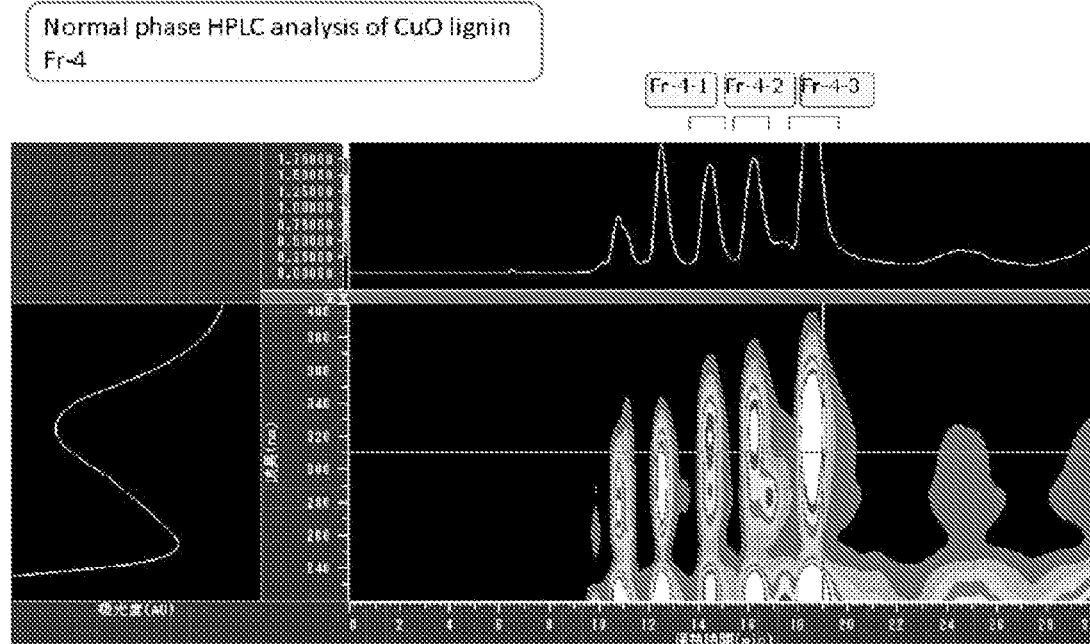
FIG. 2 includes charts, showing a result of normal phase HPLC analysis of Fr-4 in Example.
Figure 3:
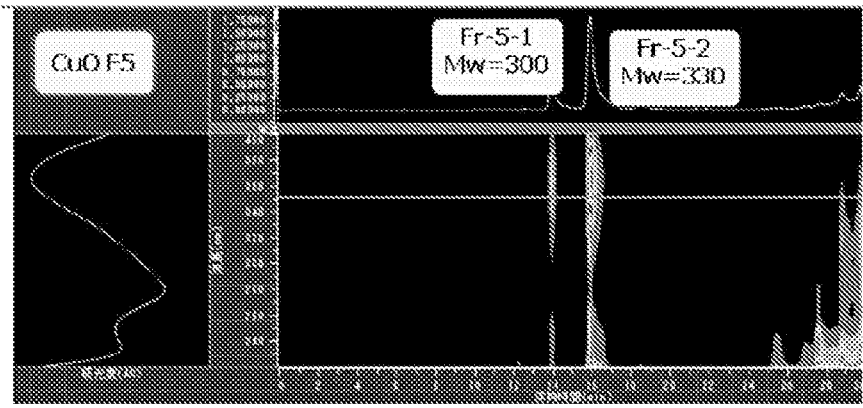
FIG. 3 includes charts, showing a result of normal phase HPLC analysis of Fr-5 in Example.
Figure 4:
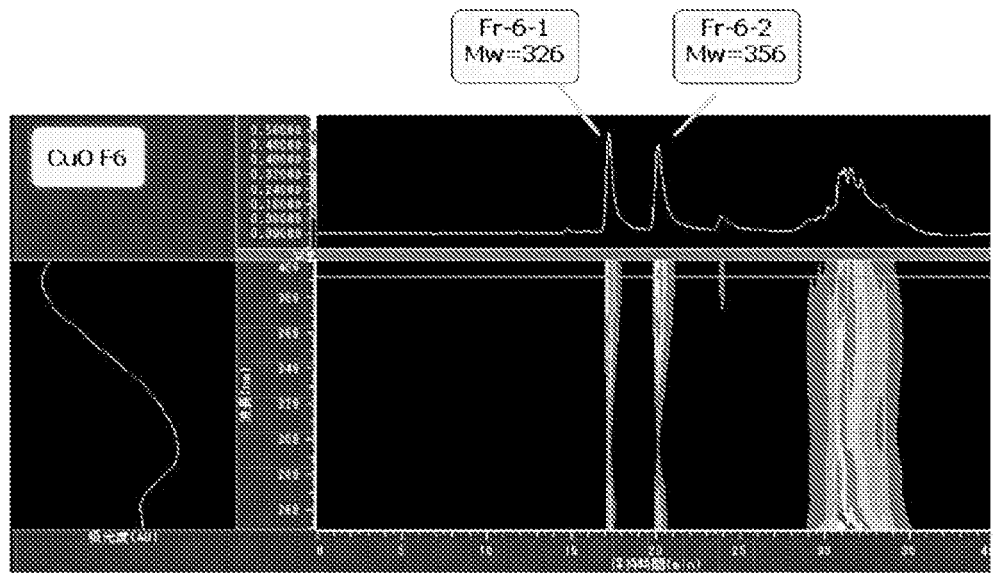
FIG. 4 includes charts, showing a result of normal phase HPLC analysis of Fr-6 in Example.

The results of the analyses of Fr-4, Fr-5 and Fr-6 through the HPLC are shown in FIG. 2 to FIG. 4.

As shown in FIG. 2 to FIG. 4, the purifications through the normal phase HPLC resulted in the isolations of compounds having the following molecular weights (Mw), which are capable of absorbing ultraviolet radiation.

From Fr-4; compound Fr-4-1 (Mw=302), compound Fr-4-2 (Mw=332) and compound Fr-4-3 (Mw=362).

From Fr-5; compound Fr-5-1 (Mw=300) and compound Fr-5-2 (Mw=330).

From Fr-6; compound Fr-6-1 (Mw=326) and compound Fr-6-2 (Mw=356).

Further, analyses for the above-described compounds were conducted by utilizing: liquid chromatography-mass spectrometry (LC-MS): gas chromatography-mass spectrometry (GC-MS): and nuclear magnetic resonance (NMR). The measurements by the NMR in the present examples were conducted under the following conditions. In addition to above, DRX600 NMR spectrometer equipped with a cryoprobe with a Zgradient (commercially available from Bruker BioSpin, Germany) was employed for the NMR analyses.

For compounds Fr-4-1 to Fr-4-3, Fr-5-1 and Fr-5-2: Proton NMR ($^1$H-NMR, 600 MHz, Solvent: deuterated acetone $(CD_3)_2CO$); and For compounds Fr-6-1 and Fr-6-2: $^1$H-NMR (600 MHz, Solvent: deuterated methanol $CD_3OD$).

Figure 5:
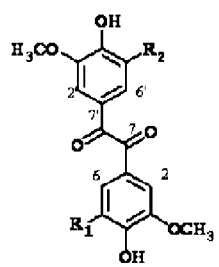
FIG. 5 includes tables, showing results of Proton NMR ($^1$H-NMR) measurements for compounds of Fr-4-1, Fr-4-2 and Fr-4-3.
Figure 6:
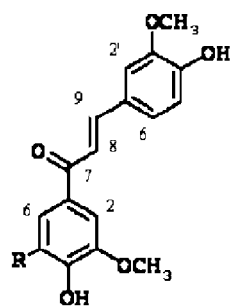
FIG. 6 includes tables, showing results of $^1$H-NMR measurements for compounds of Fr-5-1 and Fr-5-2.
Figure 7:
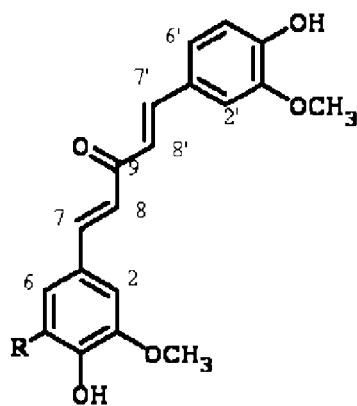
FIG. 7 includes tables, showing results of $^1$H-NMR measurements for compounds of Fr-6-1 and Fr-6-2.

The results of the NMR measurements for the compounds obtained from Fr-4 to Fr-6 are shown in FIG. 5 to FIG. 7, respectively.

Further, the results of the LC-MS measurements for the respective compounds are as follows. In addition to above, LCMS-2010A (commercially available from Shimadzu Corporation) was employed for the LC-MS.

Compound Fr-4-1: LC-MS (atmospheric pressure chemical ionization (APCI)-negative) mass-to-charge ratio (m/z)=301.

Compound Fr-4-2: LC-MS (APCI-negative) m/z=331.

Compound Fr-4-3: LC-MS (APCI-negative) m/z=361.

Compound Fr-5-1: LC-MS (APCI-negative) m/z=299.

Compound Fr-5-2: LC-MS (APCI-negative) m/z=329.

Compound Fr-6-1: LC-MS (APCI-negative) m/z=325.

Compound Fr-6-2: LC-MS (APCI-negative) m/z=355.

According to FIG. 2 to FIG. 7, it was found that the compounds obtained from the respective fractions were respectively identified as the following compounds.

Specifically, the compound Fr-5-2, among the compounds extracted from Fr-5, was identified as the compound shown in the above Formula (1-1), and the compound Fr-6-2, among the compounds extracted from Fr-6, was identified as the compound shown in the above Formula (1-2).

[Chem. 8]

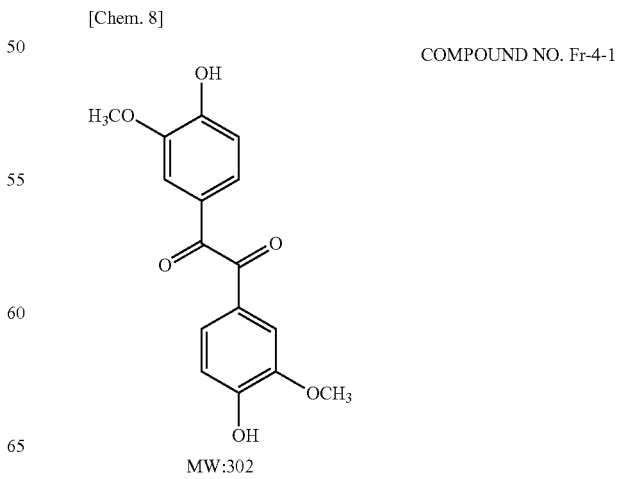

COMPOUND NO. Fr-4-1

Fr-4-2
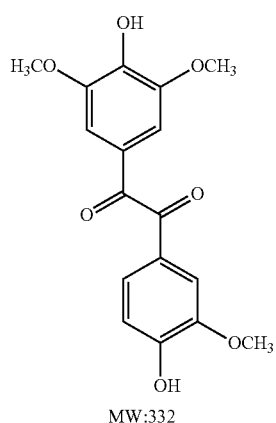
MW:332
Fr-4-3
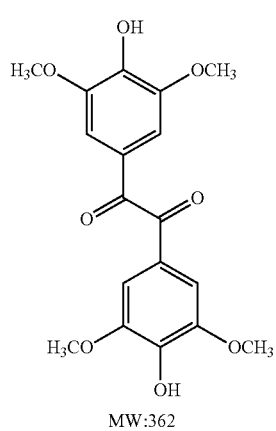
MW:362
COMPOUND NO. Fr-5-1
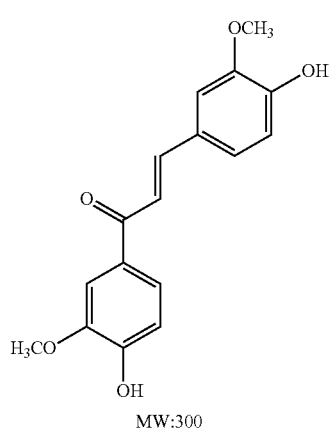
MW:300
Fr-5-2
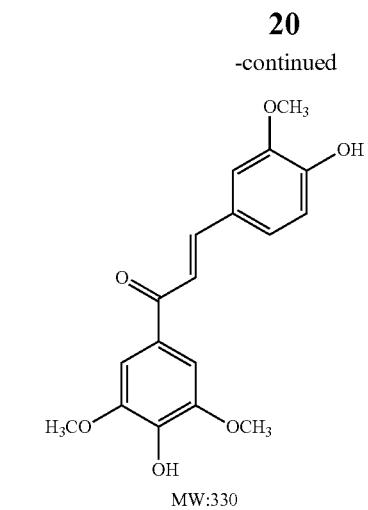
MW:330
Fr-6-1
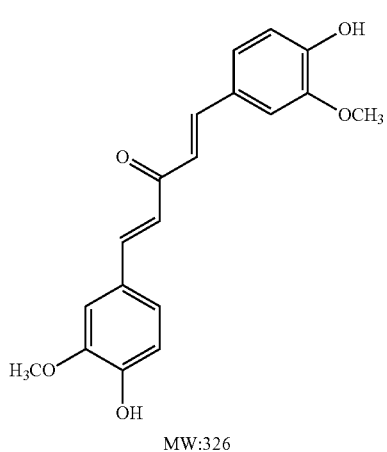
MW:326
Fr-6-2
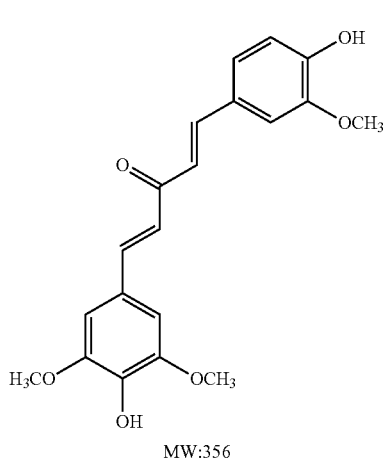
MW:356

Figure 8:
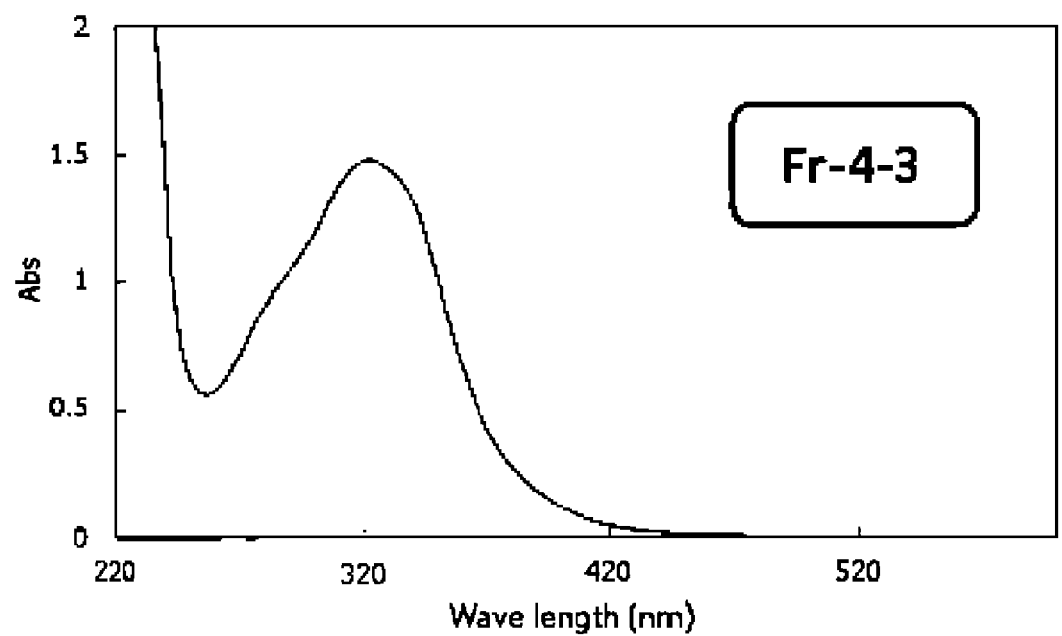
FIG. 8 is a graph, showing a result of a measurement of ultraviolet absorption spectrum for a compound of Fr-4-3.
Figure 9:
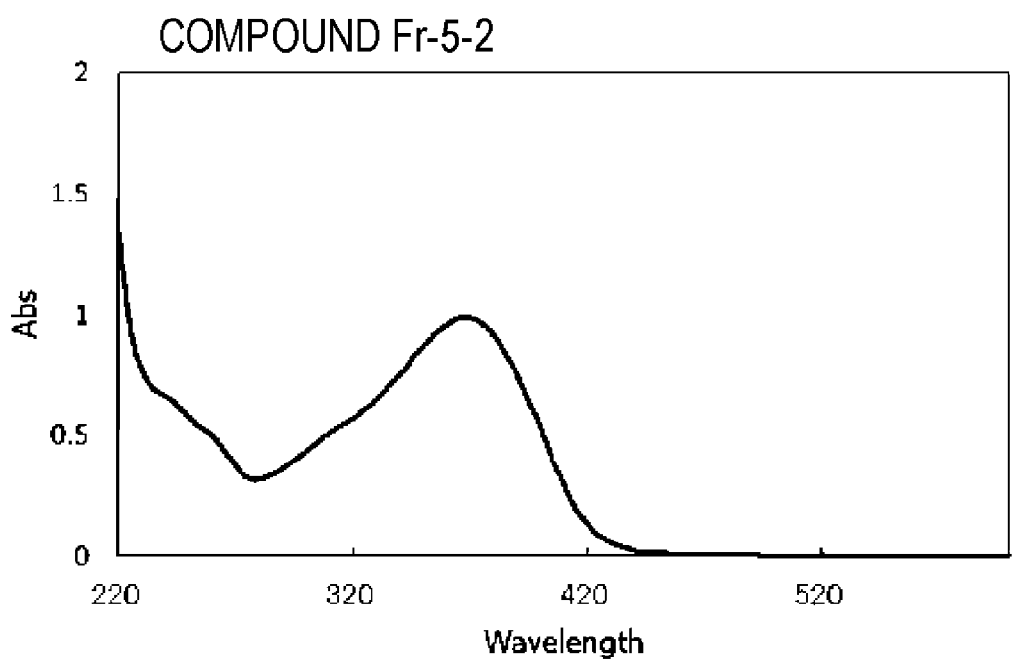
FIG. 9 includes graphs (a) and (b), showing results of measurements of ultraviolet absorption spectra for a compound of Fr-5-2 and Fr-6-2, respectively.
Figure 9:
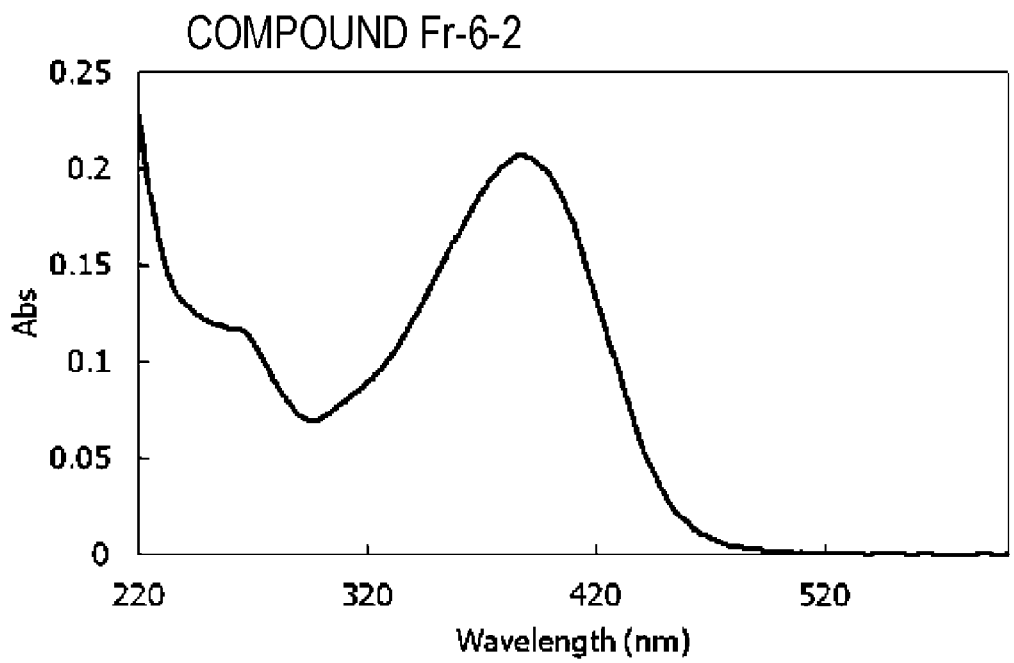

Further, the results of the measurements of the ultraviolet absorption spectra for the compound Fr-4-3, the compound Fr-5-2 and the compound Fr-6-2 are shown in FIG. 8 and FIG. 9, respectively. The conditions for the measurements of the ultraviolet absorption spectra were as follows.

(UV Measurement Conditions)

Measuring equipment; spectral photometer U3310, commercially available from Hitachi Co., Ltd.

Solvent: methanol (neutral).

Concentrations: 20 to 25 ppm for the compound Fr-4-3; 20 to 25 ppm for the compound Fr-5-2; and 5 ppm for the compound Fr-6-2.

Example 2

In the present example, the oxidative degradations of Siebold's beech (*Fagus crenata*) with nitrobenzene were conducted to obtain the respective compounds. 1.0 g of the fraction of the Siebold's beech (*Fagus crenata*) wood powder passing through 42 mesh sieve (Japanese Industrial Standards), 1 mL of nitrobenzene, and 16 mL of 2N NaOH aqueous solution were introduced to a pressure tight glass vessel, and after the seal was provided, the vessel was exposed to the microwave of 2,450 MHz at 180 degrees C. for 30 minutes by using a microwave processing apparatus. The resultant processed liquid was cooled, and then, a centrifugal separation process (employing CF25RXII, commercially available from Hitachi Co., Ltd., 6,000 rpm, for 3 minutes) and a reduced pressure filtration process were conducted to achieve a separation into an alkaline-soluble fraction and an insoluble fraction.

The alkaline-soluble fraction thereof was treated with diethyl ether to extract and remove nitrobenzene or the like, and then was further treated with 1N HCl to adjust its acidity as pH 1.5, and an extraction with ethyl acetate was conducted to obtain a low molecular weight lignin fraction.

The obtained low molecular weight lignin fraction was treated according to the method described in Example 1 to separate the respective fractions having UV absorption bands, and then analyses by reversed phase HPLC-MS were conducted. The results of the analyses indicated that the compounds of Fr-4-1, Fr-4-2, Fr-4-3, Fr-5-1 and Fr-5-2 as described above in Example 1 were detected as the compounds isolated from the low molecular weight fraction of the wood powder of *Fagus crenata* through copper oxide-degradation.

Example 3

In the present example, the copper oxide degradations of the *Cryptomeria japonica* (Cryptomeria) were conducted to obtain the respective compounds. The copper oxide degradations of the fraction of the *Cryptomeria japonica* wood powder passing through 42 mesh sieve (Japanese Industrial Standards) were conducted according to the method described in Example 1. The material balance obtained by conducting the fractionation is shown in Table 3.

TABLE 3

MATERIAL BALANCE OF COPPER OXIDE DEGRADED PRODUCTS OF *CRYPTOMERIA JAPONICA*

| | ALIS (mg) | ACIS (mg) | ACSL (mg) |
| --- | --- | --- | --- |
| *Cryptomeria japonica* | 1008 | 125 | 58 |

Further, the low molecular weight lignin fraction was treated according to the method described in Example 1 to separate the respective fractions having UV absorption bands, and then analyses by reversed phase HPLC-MS were conducted. The results of the analyses indicated that the compounds of Fr-4-1, Fr-5-1 and Fr-6-1 as described above in Example 1 were detected.

The invention claimed is:

1. A compound represented by the following General Formula (1)

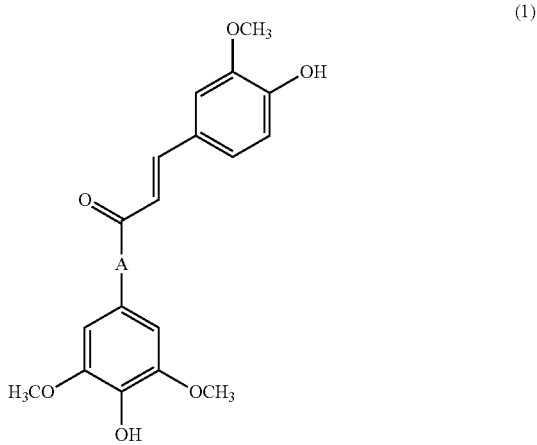

wherein, in the above General Formula (1), A is a single bond or —C═C— group.

2. An ultraviolet (UV) absorber, comprising the compound according to claim 1 and at least one compound selected from the group consisting of a compound represented by the following General Formula (2) a compound represented by the following General Formula (3) and a compound represented by the following General Formula (4)

(2)

wherein, in the above General Formula (2), $R^1$ and $R^2$ are a hydrogen atom or a —OCH$_3$ group, and are mutually independent, (3)

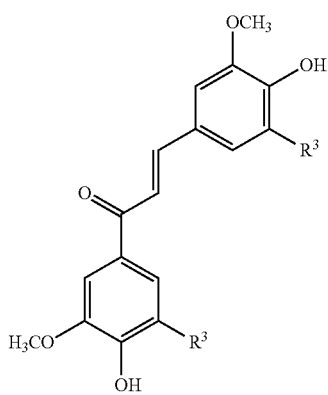

wherein, in the above General Formula (3), $R^3$ is a hydrogen atom or a —$OCH_3$ group, (4)

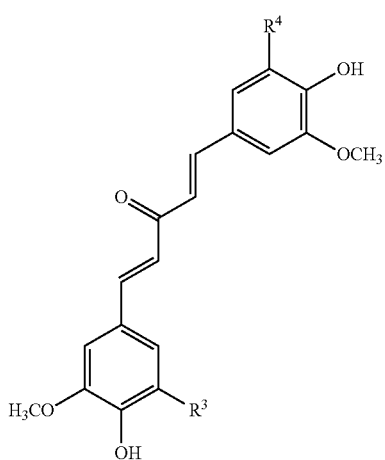

wherein, in the above General Formula (4), $R^4$ is a hydrogen atom or a —$OCH_3$ group.

3. The UV absorber according to claim 2, comprising the following compounds Fr-5-2 and Fr-6-2

(Fr-5-2)

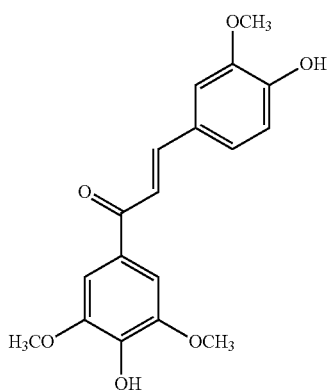

(Fr-6-2)

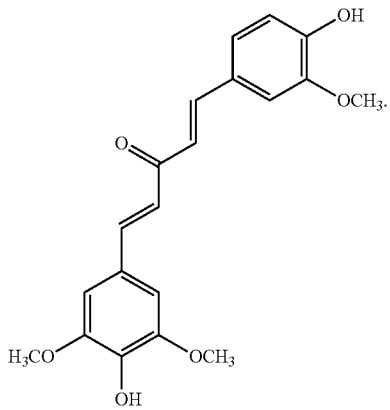

4. The UV absorber according to claim 2, comprising the following compounds Fr-6-2 and Fr-4-1

(Fr-6-2)

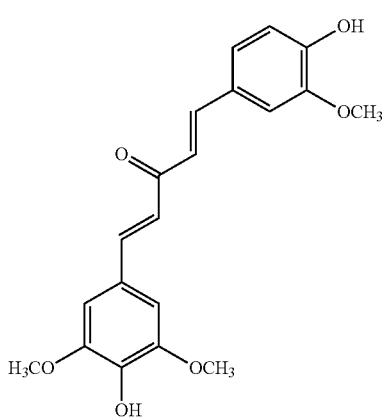

(Fr-4-1)

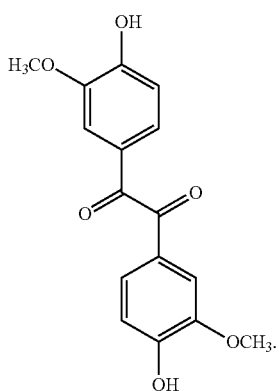

5. The UV absorber according to claim 2, comprising the following compounds Fr-5-2 and Fr-4-

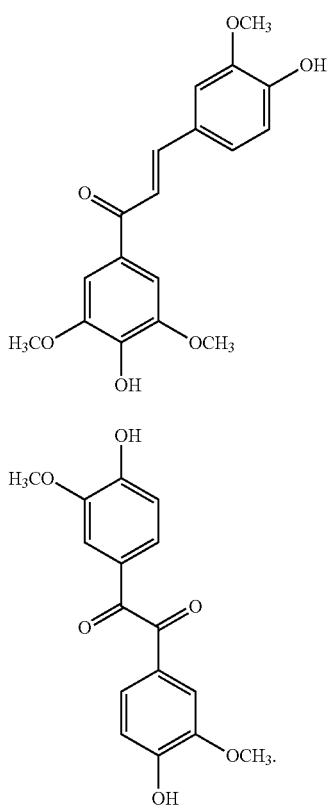
(Fr-5-2)
(Fr-4-1)
6. The UV absorber according to claim 2, comprising the following compounds Fr-6-2 and Fr-4-2
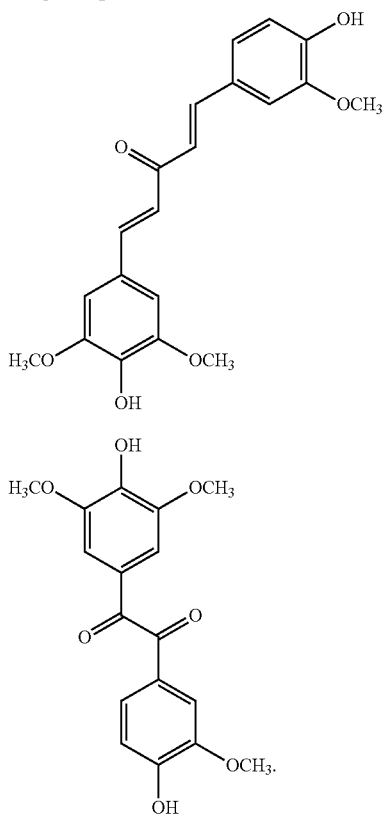
(Fr-6-2)
(Fr-4-2)
7. The UV absorber according to claim 2, comprising the following compounds Fr-5-2 and Fr-4-2
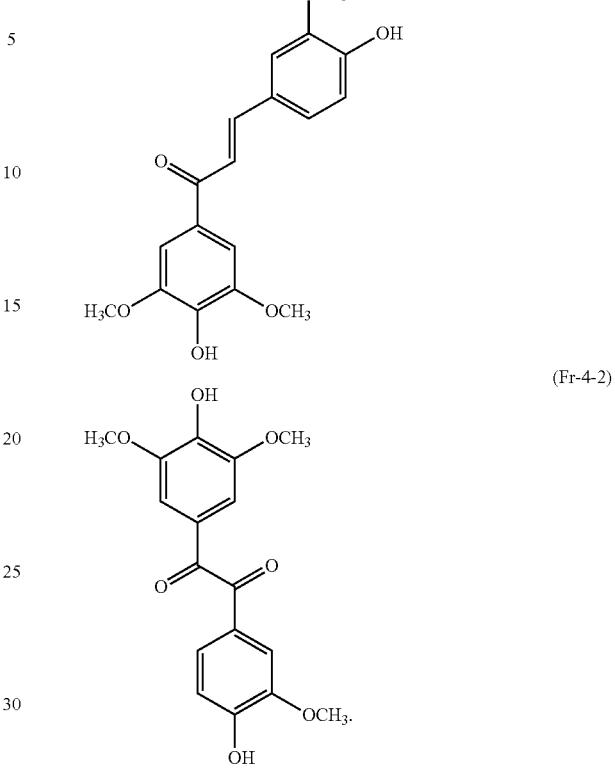
(Fr-5-2)
(Fr-4-2)
8. The UV absorber according to claim 2, comprising the following compounds Fr-6-2 and Fr-4-3
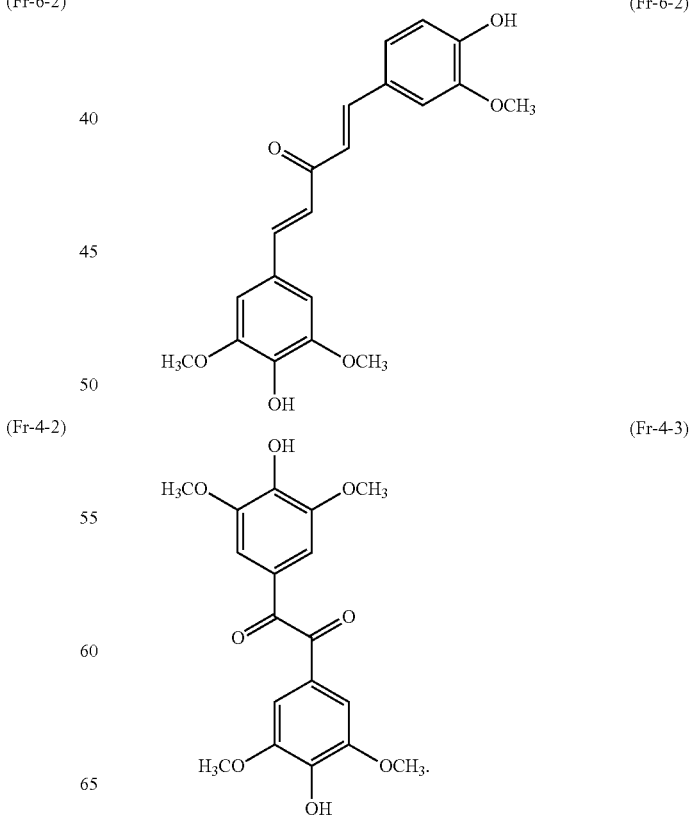
(Fr-6-2)
(Fr-4-3)

9. The UV absorber according to claim 2, comprising the following compounds Fr-5-2 and Fr-4-3
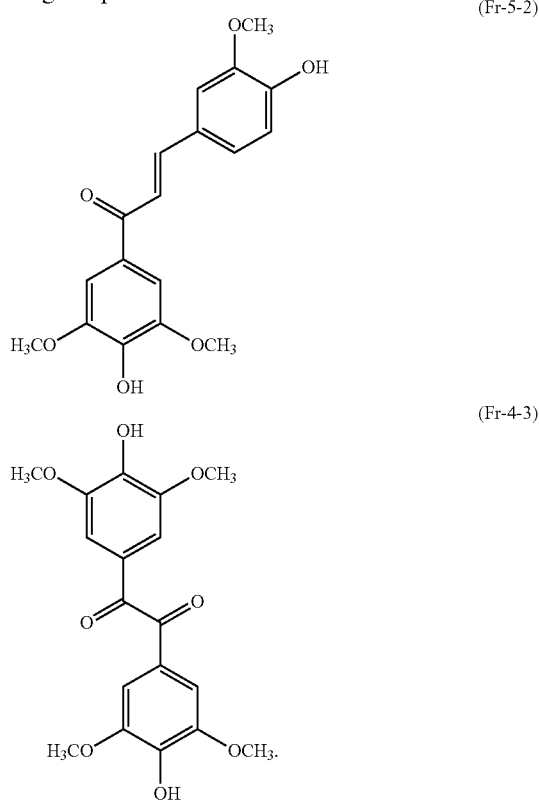
10. The UV absorber according to claim 2, comprising the following compounds Fr-6-2 and Fr-5-1
11. The UV absorber according to claim 2, comprising the following compounds Fr-5-2 and Fr-5-1
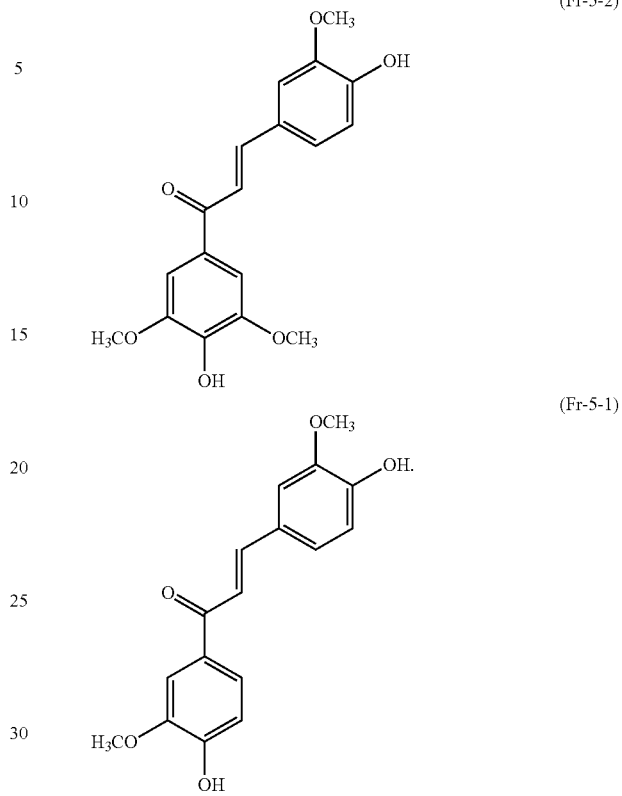
12. The UV absorber according to claim 2, comprising the following compounds Fr-6-2 and Fr-6-1
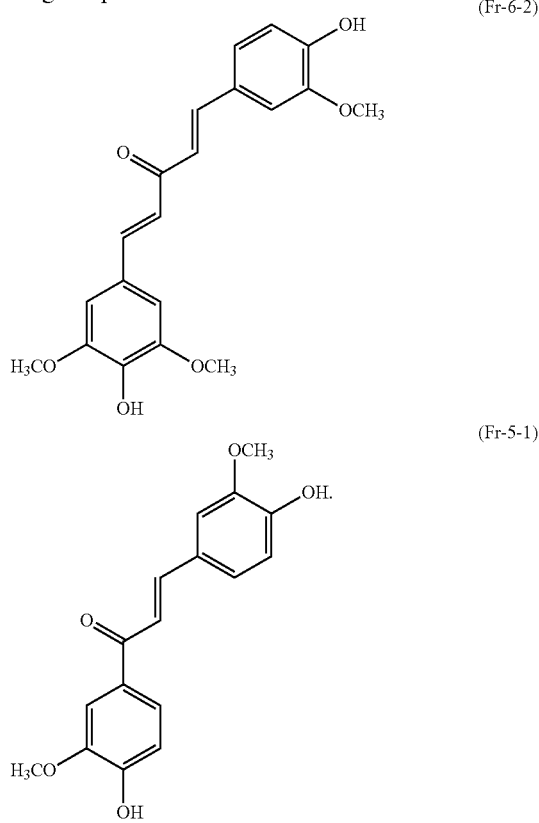
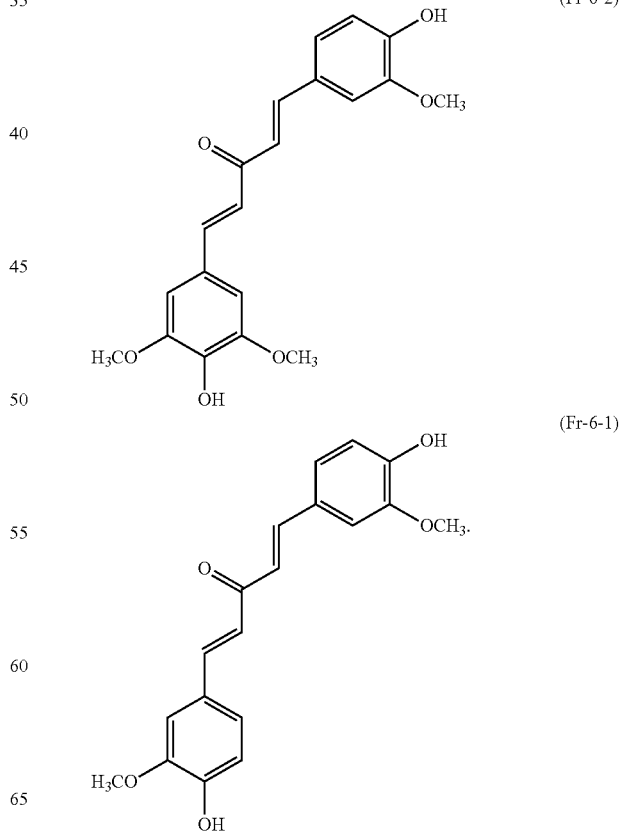

13. The UV absorber according to claim 2, comprising the following compounds Fr-5-2 and Fr-6-1
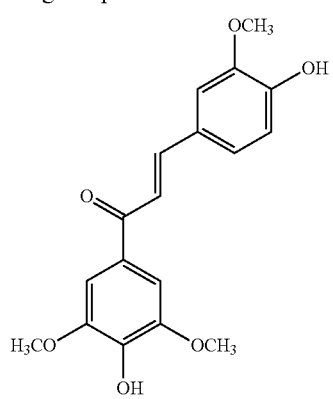
(Fr-5-2)
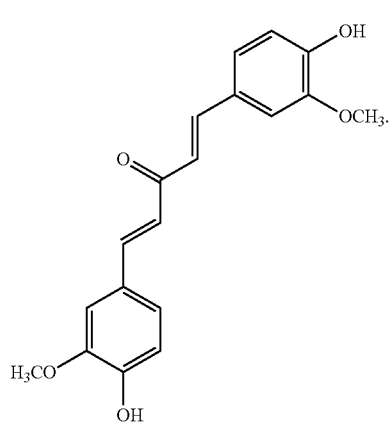
(Fr-6-1)
14. The UV absorber according to claim 2, comprising the following compounds Fr-5-2, Fr-4-1, Fr-4-2 and Fr-4-3
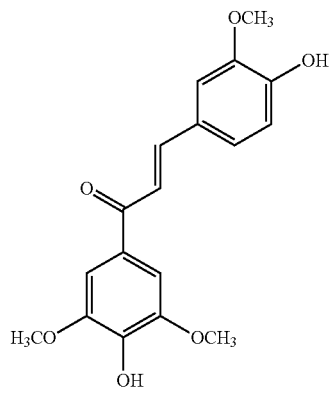
(Fr-5-2)
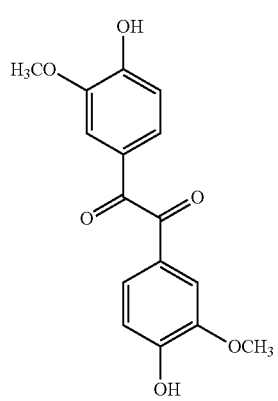
(Fr-4-1)
-continued
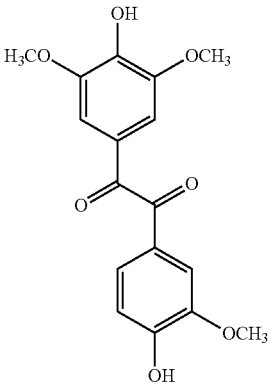
(Fr-4-2)
(Fr-4-3)
15. The UV absorber according to claim 2, comprising the following compounds Fr-6-2, Fr-4-1, Fr-4-2 and Fr-4-3
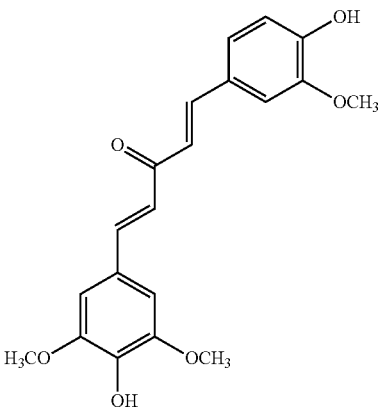
(Fr-6-2)
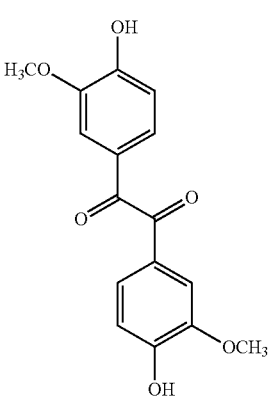
(Fr-4-1)

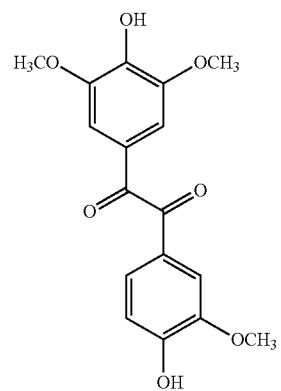
(Fr-4-2)
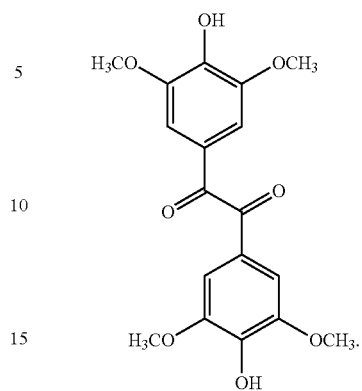
(Fr-4-3)
* * * * *